(12) United States Patent
Huang et al.

(10) Patent No.: US 8,809,018 B2
(45) Date of Patent: Aug. 19, 2014

(54) MODIFIED NUCLEOTIDE MOLECULES OF XYLANASE AND APPLICATION THEREOF

(75) Inventors: Yahui Huang, Hsinchu (TW); Chunhui Hsieh, Ershui Township, Changhua County (TW)

(73) Assignee: YFY Biopulp Technology Limited, Tortola (VG)

( * ) Notice: Subject to any disclaimer, the term of this patent is extended or adjusted under 35 U.S.C. 154(b) by 158 days.

(21) Appl. No.: 13/513,952

(22) PCT Filed: Feb. 10, 2010

(86) PCT No.: PCT/CN2010/070602
§ 371 (c)(1),
(2), (4) Date: Jun. 5, 2012

(87) PCT Pub. No.: WO2011/097792
PCT Pub. Date: Aug. 18, 2011

(65) Prior Publication Data
US 2012/0288915 A1    Nov. 15, 2012

(51) Int. Cl.
| | |
|---|---|
| C12P 21/06 | (2006.01) |
| C12N 9/00 | (2006.01) |
| C12N 9/24 | (2006.01) |
| C12N 1/20 | (2006.01) |
| C12N 15/00 | (2006.01) |
| C07H 21/04 | (2006.01) |

(52) U.S. Cl.
USPC ....... 435/69.1; 435/183; 435/200; 435/252.3; 435/320.1; 536/23.2

(58) Field of Classification Search
None
See application file for complete search history.

(56) References Cited

FOREIGN PATENT DOCUMENTS

| | | | |
|---|---|---|---|
| CN | 101413002 A | 4/2009 | |
| TW | 200720435 | 6/2007 | ............... C12N 9/00 |
| WO | 2008017646 A2 | 2/2008 | |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Accession AXC18018. Jun. 1, 2007.*
Wang Y, Yao B, Huang H, *N. frontalis* xylanase sequence, European Bioinformatics Institute Data Base Accession No. DQ517886 (2006).
Singh A, et al., "*Saccharomyces cerevisiae* contains two discrete genes coding for the α-factor pheromone", Nucleic Acids Research (1983), pp. 4049-4063, vol. 11, No. 12, IRL Press Limited, Oxford, England.
Chang Ting Tsai, et al., "Overexpression of the *Neocallimastix frontalis* xylanase gene in the methylotrophic yeasts *Pichia pastoris* and *Pichia methanolica*", Enzyme and Microbial Technology (2008), pp. 459-465, vol. 42, No. 6, Elsevier Science.
European Search Report and Search Opinion, Jul. 11, 2013.
Trinci et al. 1994, Anaerobic fungi in herbivorous animals, Mycol. Res., 98:129-152.
Romanos et al. 1992, Foreign Gene Expression in Yeast: A Review, Yeast, 8:423-488.
Sharp et al. 1986, Codon usage in yeast: cluster analysis clearly differentiates highly and lowly expressed genes, Nucleic Acids Res., 14:5125-5143.
Micheelsen et al., 2008, High-level expression of the native barley ?-amylase/subtilisin inhibitor in *Pichia pastoris*, Journal of Biotechnology, 133:424-432.
Georis et al., 1999, Sequence, overproduction and purification of the family 11 endo-beta-1,4-xylanase encoded by the xyl1 gene of *Streptomyces* sp. S38, Gene 237:123-33.
Sambrook et al., 2001, Molecular Cloning: SDS-polyacrylamide gel electrophoresis of protein, Third edition: A8. 40-49.

* cited by examiner

*Primary Examiner* — Christian Fronda
(74) *Attorney, Agent, or Firm* — Michael W. Ferrell; Ferrells, PLLC; Anna L. Kinney (57) ABSTRACT

Modified nucleotide molecules of xylanase and the application of the nucleotide molecules in constructing recombinant vectors, host cells or producing xylanase are disclosed, wherein the nucleotide molecules contain nucleotide sequences having greater than 80% identity with nucleotide sequence shown by SEQ ID NO: 1.

12 Claims, 3 Drawing Sheets

```
              10        20        30        40        50        60        70
         ....|....|....|....|....|....|....|....|....|....|....|....|....|....|
xyn11B'    1 ACTGTTGCTAAGGCCCAATGGGGTGGAGGTGCTTCCGCTGGTCAAAAATTATCCGTCGGTGGTGGTCAAA 70
             T  V  A  K  A  Q  W  G  G  G  A  S  A  G  Q  K  L  S  V  G  G  G  Q
coxyn11B'  1 ........T........T........T............G..G..T..T............ 70
             T  V  A  K  A  Q  W  G  G  G  A  S  A  G  Q  K  L  S  V  G  G  G  Q 80        90       100       110       120       130       140
         ....|....|....|....|....|....|....|....|....|....|....|....|....|....|
xyn11B'   71 ACCAACATAAGGGTGTCTCCGATGGTTTCAGTTATGAAATCTGGTTAGATAACACCGGTGGTAGCGGTTC 140
             N  Q  H  K  G  V  S  D  G  F  S  Y  E  I  W  L  D  N  T  G  G  S  G  S
coxyn11B' 71 .......C........T..T..C......TC...C.........G..C.....T......TCT..... 140
             N  Q  H  K  G  V  S  D  G  F  S  Y  E  I  W  L  D  N  T  G  G  S  G  S 150       160       170       180       190       200       210
         ....|....|....|....|....|....|....|....|....|....|....|....|....|....|
xyn11B'  141 TATGACTCTCGGTAGTGGTGCAACCTTCAAGGCTGAATGGAATGCAGCTGTTAACCGTGGTAACTTCCTT 210
             M  T  L  G  S  G  A  T  F  K  A  E  W  N  A  A  V  N  R  G  N  F  L
coxyn11B'141 .......T.G...TC......T..T................C..T.........A..A.........T.G 210
             M  T  L  G  S  G  A  T  F  K  A  E  W  N  A  A  V  N  R  G  N  F  L 220       230       240       250       260       270       280
         ....|....|....|....|....|....|....|....|....|....|....|....|....|....|
xyn11B'  211 GCCCGTCGTGGTCTTGACTTCGGTTCTCAAAAGAAGGCAACCGATTACAGCTACATCGGATTGGATTATA 280
             A  R  R  G  L  D  F  G  S  Q  K  K  A  T  D  Y  S  Y  I  G  L  D  Y
coxyn11B'211 ..TA.AA.A..T.A................T..T..C...TCT.......T..A..C..C. 280
             A  R  R  G  L  D  F  G  S  Q  K  K  A  T  D  Y  S  Y  I  G  L  D  Y 290       300       310       320       330       340       350
         ....|....|....|....|....|....|....|....|....|....|....|....|....|....|
xyn11B'  281 CTGCAACTTACAGACAAACTGCCAGTGCAAGTGGTAACTCCCGTCTCTGTGTATACGGATGGTTCCAAAA 350
             T  A  T  Y  R  Q  T  A  S  A  S  G  N  S  R  L  C  V  Y  G  W  F  Q  N
coxyn11B'281 .....T..............TTC...TTC.........TA.AT.G.....T.....T.......... 350
             T  A  T  Y  R  Q  T  A  S  A  S  G  N  S  R  L  C  V  Y  G  W  F  Q  N 360       370       380       390       400       410       420
         ....|....|....|....|....|....|....|....|....|....|....|....|....|....|
xyn11B'  351 CCGTGGAGTTCAAGGCGTTCCTTTAGTAGAATACTACATCATTGAAGATTGGGTTGACTGGGTTCCAGAT 420
             R  G  V  Q  G  V  P  L  V  E  Y  Y  I  I  E  D  W  V  D  W  V  P  D
coxyn11B'351 .A.A..T........T.....A..G..T.............C.................... 420
             R  G  V  Q  G  V  P  L  V  E  Y  Y  I  I  E  D  W  V  D  W  V  P  D
```

FIG. 1

```
                    430       440       450       460       470       480       490
                ....|....|....|....|....|....|....|....|....|....|....|....|....|....|
xyn11B'     421 GCACAAGGAAAAATGGTAACCATCGATGGAGCTCAATATAAGATTTTCCAAATGGATCACACTGGTCCAA 490
                 A  Q  G  K  M  V  T  I  D  G  A  Q  Y  K  I  F  Q  M  D  H  T  G  P
coxyn11B'   421 ..T.....T..G.....T..T......C..T..........C......C...............    490
                 A  Q  G  K  M  V  T  I  D  G  A  Q  Y  K  I  F  Q  M  D  H  T  G  P 500       510       520       530       540       550       560
                ....|....|....|....|....|....|....|....|....|....|....|....|....|....|
xyn11B'     491 CTATCAATGGTGGTAGTGAAACCTTTAAGCAATACTTCAGTGTCCGTCAACAAAAGAGAACTTCTGGTCA 560
                 T  I  N  G  G  S  E  T  F  K  Q  Y  F  S  V  R  Q  Q  K  R  T  S  G  H
coxyn11B'   491 ....T..C......TC......T..C............TC...TA.A..................    560
                 T  I  N  G  G  S  E  T  F  K  Q  Y  F  S  V  R  Q  Q  K  R  T  S  G  H 570       580       590       600       610       620       630
                ....|....|....|....|....|....|....|....|....|....|....|....|....|....|
xyn11B'     561 TATTACTGTCTCAGATCACTTTAAGGAATGGGCTAAGCAAGGTTGGGGTATTGGTAACCTTTATGAAGTT 630
                 I  T  V  S  D  H  F  K  E  W  A  K  Q  G  W  G  I  G  N  L  Y  E  V
coxyn11B'   561 C..C.....T..T..C.....C................C......T..G..C......            630
                 I  T  V  S  D  H  F  K  E  W  A  K  Q  G  W  G  I  G  N  L  Y  E  V 640       650       660       670       680       690       700
                ....|....|....|....|....|....|....|....|....|....|....|....|....|....|
xyn11B'     631 GCTTTGAACGCCGAAGGTTGGCAAAGTAGTGGTGTTGCTGATGTCACCTTATTAGATGTTTACACAACTC 700
                 A  L  N  A  E  G  W  Q  S  S  G  V  A  D  V  T  L  L  D  V  Y  T  T
coxyn11B'   631 ...........T............TC.TC..........C..T..T..G..G..C........T....  700
                 A  L  N  A  E  G  W  Q  S  S  G  V  A  D  V  T  L  L  D  V  Y  T  T 710       720
                ....|....|....|....|
xyn11B'     701 CAAAGGGTTCTAGTCCAGCG 720
                 P  K  G  S  S  P  A
coxyn11B'   701 ...........TC.......  720
                 P  K  G  S  S  P  A
```

FIG. 1-*Continue*

```
            10        20        30        40        50        60        70
    ....|....|....|....|....|....|....|....|....|....|....|....|....|....|
αF  1  ATGAGATTTCCTTCAATTTTTACTGCTGTGTTTATTCGCAGCATCCTCCGCATTAGCTGCTCCAGTCAACA 70
       M  R  F  P  S  I  F  T  A  V  L  F  A  A  S  S  A  L  A  A  P  V  N
coαF 1 ........C..A..T..C..C...........G........T..T..T..T..T..............T.... 70
       M  R  F  P  S  I  F  T  A  V  L  F  A  A  S  S  A  L  A  A  P  V  N 80        90        100       110       120       130       140
    ....|....|....|....|....|....|....|....|....|....|....|....|....|....|
αF  71 CTACAACAGAAGATGAAACGGCACAAATTCCGGCTGAAGCTGTCATCGGTTACTCAGATTTAGAAGGGGA 140
       T  T  T  E  D  E  T  A  Q  I  P  A  E  A  V  I  G  Y  S  D  L  E  G  D
coαF 71 ....T..T............T..T.....C..A...........T...........T..C..G.....T.. 140
       T  T  T  E  D  E  T  A  Q  I  P  A  E  A  V  I  G  Y  S  D  L  E  G  D 150       160       170       180       190       200       210
    ....|....|....|....|....|....|....|....|....|....|....|....|....|....|
αF  141 TTTCGATGTTGCTGTTTTGCCATTTTCCAACAGCACAAATAACGGGTTATTGTTTATAAATACTACTATT 210
        F  D  V  A  V  L  P  F  S  N  S  T  N  N  G  L  L  F  I  N  T  T  I
coαF 141 ......C................C..T...TCA..T..C.....T..G.....C..C..C........C 210
        F  D  V  A  V  L  P  F  S  N  S  T  N  N  G  L  L  F  I  N  T  T  I 220       230       240       250       260
    ....|....|....|....|....|....|....|....|....|....|....|..
αF  211 GCCAGCATTGCTGCTAAAGAAGAAGGGGTATCTCTCGAGAAAAGAGAGGCTGAAGCT 267
        A  S  I  A  A  K  E  E  G  V  S  L  E  K  R  E  A  E  A
coαF 211 ..TTCT..C........G........T..T...T.G..A..G.....A......... 267
        A  S  I  A  A  K  E  E  G  V  S  L  E  K  R  E  A  E  A
```

MODIFIED NUCLEOTIDE MOLECULES OF XYLANASE AND APPLICATION THEREOF

This application claims priority to PCT Patent Application No. PCT/CN2010/070602, filed on Feb. 10, 2010, the disclosure of which is incorporated by reference.

CROSS-REFERENCES TO RELATED APPLICATIONS

Not applicable.

BACKGROUND OF THE INVENTION

1. Field of the Invention

The present invention relates to a modified nucleotide molecule of xylanase and use thereof, especially to a method for producing xylanase using the nucleotide molecule.

2. Descriptions of the Related Art

Xylanase is a main enzyme decomposing hemicelluloses among carbohydrate hydrolysis enzymes. Xylanase can be widely used, e.g., in food, in animal feed compositions, in textile or in papermaking applications, etc. For example, xylanase can be used to treat feeds for poultry to promote the break-down of anti-nutritional factors in feeds, which leads to better utilization of the nutrients and improving the growth of poultry. In addition, when added to dough, xylanase improves the mechanical strength of the dough, thereby, improving the lightness and storability of the flour products.

For known xylanases from different origins, xylanases from anaerobic fungi, also called rumen fungi, are gaining more attention in that anaerobic fungi usually live in the highly competitive environment of the rumen (such as the digestive tracts of ruminants and monogastric herbivores); therefore, these microorganisms evolve to yield enzymes with high activity (see Trinci et al. 1994. Anaerobic fungi in herbivorous animals. *Mycol. Res.* 98:129-152., which is incorporated hereinto by reference).

In view of extensive utilization, xylanases of anaerobic fungi are in great demand in various fields; however, due to the limitations of culture techniques of anaerobic fungi and slow growth rate of fungi, mass production through a natural cultivation method cannot be achieved, and thus, the use of xylanases from anaerobic fungi is hindered. Therefore, the above problem may be solved if a gene cloning method and an easily operable host cell can be utilized to express xylanases from anaerobic fungi.

Some yeasts have advantages, such as a rapid cell growth rate, suitability for high cell density cultivations, utilization of methanol as a carbon source, etc, and thus, it has been suggested in the literature that the production of recombinant proteins in a great amount can be achieved using yeasts as host cells (see Romanos et al. 1992. Foreign Gene Expression in Yeast: A Review. Yeast 8:423-488., which is incorporated hereinto by reference). However, in the industry, xylanase production on a factory scale is needed for application in various household or industrial use; for academia, a great amount of xylanase is needed for scientific research. Therefore, the above described cloning techniques still fail to reach the demand for a large-scale production of xylanase in industry or academia. As a result, a method for the mass production of a desired xylanase by enhancing the expression efficiency of host cells is in great demand.

The present invention is in response to those demands, utilizing molecular biology techniques of gene cloning to produce xylanases with high activity and thermo-tolerance. The inventors of the present application found that the level of xylanase expression can be considerably increased through the modification of a specific gene of xylanase.

SUMMARY OF THE INVENTION

The primary objective of this invention is to provide an isolated nucleotide molecule comprising a nucleotide sequence encoding xylanase and having a sequence homology of at least 80% to the nucleotide sequence of SEQ ID NO:1.

Another objective of this invention is to provide a recombinant vector which comprises (a) a vector and (b) a nucleotide molecule comprising at least one of the following nucleotide sequences: (b1) a nucleotide sequence encoding xylanase and having a sequence homology of at least 80% to the nucleotide sequence of SEQ ID NO:1, and (b2) a nucleotide sequence encoding a secreting protein signal peptide and having a sequence homology of at least 80% to the nucleotide sequence of SEQ ID NO:2.

Yet a further objective of this invention is to provide a *Pichia methanolica* host cell which comprises the nucleotide molecule or recombinant vector of the present invention.

Still a further objective of this invention is to provide a method for producing xylanase which comprises the following steps: (1) transforming a recombinant vector expressing xylanase to a *Pichia methanolica* host cell; and (2) incubating the *Pichia methanolica* host cell to express the xylanase.

The detailed technology and preferred embodiments implemented for the subject invention are described in the following paragraphs accompanying the appended drawings for people skilled in this field to well appreciate the features of the claimed invention.

DETAILED DESCRIPTION OF THE INVENTION

Unless otherwise stated herein, the terms "a (an)", "the" or the like used in this specification (especially in the Claims hereinafter) shall be understood to encompass both the singular form and the plural form.

As known to people skilled in the art of biology, a codon is composed of three nucleotides, wherein there are four types of nucleotides: adenine, A; guanine, G; cytosine, C; and thymine, T. These four nucleotides make 64 different codons (including three stop codons), which code for 20 different amino acids.

There are codon usage preferences among various microorganisms. For example, Alanine can be encoded by four different codons: GCT, GCC, GCA, and GCG. However, one microorganism may recognize codon GCT better, but another microorganism may tend to recognize codon GCC.

Microorganisms usually exhibit stronger codon usage preference for highly expressed genes (see Sharp et al. 1986. Codon usage in yeast: cluster analysis clearly differentiates highly and lowly expressed genes. *Nucleic Acids Res.* 14:5125-5143., which is incorporated hereinto by reference). Therefore, by adjusting the heterologous gene of a target protein to match the preferred codon usage of a host (or an expression system) or be easily recognized by the host, the expression efficiency of the target protein by the host can be enhanced. The modification process on a heterologous gene for a specific host described above is called "gene optimization."

The host cells which are commonly used in the art of biological techniques include prokaryotes, such as *Escherichia coli* and *Bacillus subtilis*, and eukaryotes, such as yeasts, animal cells and plant cells. Among these host cells, methylotrophic yeasts can be used as a high-efficiency expression system due to advantages, such as a rapid cell growth rate, suitability for high cell density cultivation and utilization of methanol as carbon source. Examples of common methylotrophic yeasts include *Candida* genus, *Pichia* genus, and *Hansenula* genus.

In the present invention, an original xylanase gene is modified to be a gene suitable for expression by a host *Pichia methanolica*. Herein, to modify/alter the original xylanase gene, suitable codons are selected based on the codon usage probability of the host *Pichia methanolica* to synthesize nucleotide molecules. In this modification manner, the host *Pichia methanolica* would more readily recognize the xylanase gene, which would result in a high level of expression of xylanase by the host.

The usage of *Pichia methanolica* as a host cell has the following advantages: (1) *Pichia methanolica* can utilize methanol as a sole carbon source; (2) AUG1 gene (alcohol utilizing gene) is the first enzyme gene in the genome of *Pichia methanolica* used for the metabolism of methanol, and therefore, AUG1 promoter can be used to drive the expression of a heterologous gene; and (3) *Pichia methanolica* can express a heterologous gene by inserting it into the genome through a non-homologous recombination manner, and thus, it is easier for screening of transformants with high copy numbers, high level expression, and high methanol utilization.

Thus, the present invention provides a modified isolated nucleotide molecule comprising a nucleotide sequence encoding xylanase and having a sequence homology of at least 80% to the nucleotide sequence of SEQ ID NO: 1. Preferably, the nucleotide sequence encoding xylanase has a sequence homology of at least 85% to the nucleotide sequence of SEQ ID NO:1, and more preferably, the nucleotide sequence encoding xylanase has a sequence homology of at least 90% to the nucleotide sequence of SEQ ID NO:1.

In an embodiment of the present invention, the best result can be obtained by using a nucleotide molecule comprising the nucleotide sequence of SEQ ID NO:1 to produce xylanase in a *Pichia methanolica* host cell. Through gene optimization, as the nucleotide sequence encoding xylanase comprised in the nucleotide molecule of the present invention has a sequence homology of 100% to the nucleotide sequence of SEQ ID NO:1, the expression efficiency of xylanase in the *Pichia methanolica* host cell can be considerably raised.

The xylanase expressed from the nucleotide molecule of the present invention can be widely used in various applications, e.g., in food, in animal feed compositions, in textile, or in papermaking, etc. When added to pulp in papermaking for example, xylanase effectively lowers the power required for grinding pulp and therefore, reduces the energy loss. In addition, a great amount of chlorine-containing bleach is usually added in the process of pulp bleaching. However, chlorine may lead to the generation of highly toxic organic chloride compounds, which raises the problem of disposing waste. It is known that if pulp is pretreated with xylanase before bleaching, the amount of chlorine-containing materials used could be effectively reduced, and the problem of waste disposal can be significantly mitigated.

For processing of pulp, a xylanase that can function under high temperature and has no activity to decompose cellulose can accelerate the reaction rate of pulp treating and prevent the destruction of cellulosic fiber. For this reason, the papermaking process can be effectively improved by choosing a xylanase which specifically hydrolyzes hemicellulose (i.e., without hydrolyzing cellulose) and is heat-tolerant.

Based on the above-mentioned consideration, in an embodiment of the present invention, the gene of xylanase from an anaerobic fungus with a high enzymatic activity, high specificity and heat-tolerance is used as a subject for modification. Specifically, in the embodiment, the modification is conducted on the xylanase gene of anaerobic fungus *Neocallimastix frontalis*. Herein, the xylanase gene of *Neocallimastix frontalis* undergoes the removal of a dockerin domain therein to further enhance the thermo-stability and enzymatic activity of xylanase. For example, the following method may be used to remove the dockerin domain of the xylanase gene. First of all, a polymerase chain reaction (PCR) is used to amplify the xylanase gene (about 1,011 bp) of *Neocallimastix frontalis*, and then the dockerin domain of the xylanase gene is removed by restriction enzymes, and the generated gap is filled by a ligase. After that, the xylanase gene without the dockerin domain (about 729 bp) is amplified through PCR, and the gene of xylanase with high enzymatic activity and thermo-stability is obtained (see Taiwan Patent Publication No. 200720435, which is incorporated hereinto by reference). In the following context, the xylanase gene of *Neocallimastix frontalis* without the dockerin domain is represented by "Xyn11B'." (SEQ ID NO:3)

The nucleotide molecule of the present invention further comprises a nucleotide sequence encoding a secreting protein signal peptide (hereinafter referred to as "a nucleotide sequence of a signal peptide") and having a sequence homology of at least 80% to the nucleotide sequence of SEQ ID NO:2. Without being limited by any theories, it is believed that by combining the nucleotide sequence of a signal peptide with a nucleotide sequence of different target proteins in a nucleotide molecule, after the expression of the nucleotide molecule, host cells can recognize the secreting protein signal peptide which is expressed from the nucleotide sequence of the signal peptide and linked with the target protein. The host cells then secrete the target protein out of the cells, thereby, increasing the amount of the target protein secreted out of the cells to elevate the extracellular expression level of the target protein. Any nucleotide molecule encoding a protein may comprise the nucleotide sequence of the signal peptide described above, for example, a nucleotide molecule encoding a protease, amylase, lipase, cellulase, or hemicellulase (such as xylosidase, arabinofuranosidase, or xylanase).

In addition, it was found that when the nucleotide sequence of a signal peptide is modified to match the preferred codon usage of a host cell and combined with a modified nucleotide sequence encoding xylanase, the xylanase synthesis rate of the host cell can be further increased, and the extracellular expression level of xylanase can be elevated. In one embodiment of the present invention, modifying the xylanase gene could increase the xylanase expression level by at least about 5-fold, and by at least about 9-fold if the xylanase gene is further combined with an optimized gene encoding the secreting protein signal peptide. Without being limited by any theories, it is believed that the gene modification method used in the present invention can apply not only to the xylanase gene but also the signal peptide gene, making a host readily recognize both the xylanase gene and signal peptide gene, thereby, achieving the synergistic effect of enhancing xylanase expression.

Preferably, the nucleotide sequence encoding the secreting protein signal peptide comprised in the nucleotide molecule of the present invention has a sequence homology of at least 85% to the nucleotide sequence of SEQ ID NO:2, and more preferably, has a sequence homology of at least 90% to the nucleotide sequence of SEQ ID NO:2. In one embodiment of the present invention, the best results can be obtained by using a nucleotide molecule comprising a nucleotide sequence of SEQ ID NO:2 to produce xylanase in a *Pichia methanolica* host cell. Through gene-optimization, as the nucleotide sequence of the signal peptide comprised in the nucleotide molecule of the present invention has a sequence homology of 100% to the nucleotide sequence of SEQ ID NO:2, the expression efficiency of xylanase in the *Pichia methanolica* host cell can be considerably raised.

In an embodiment of the present invention, a gene encoding a secreting protein signal peptide, α-factor signal peptide (hereinafter referred to as "αF") from *Saccharomyces cerevisiae* is used as a nucleotide sequence of a signal peptide and is modified. Then, the modified αF gene is combined with a modified nucleotide sequence encoding xylanase to provide the desired effect in elevating expression level. Herein, using the secreting protein signal peptide (i.e., αF; SEQ ID NO:4) of *Saccharomyces cerevisiae* to guide a target protein for extracellular secretion can increase the efficiency for the purification and recovery of the target protein. Related techniques can be seen in Micheelsen et al. 2008. High-level expression of the native barley α-amylase/subtilisin inhibitor in *Pichia pastoris*. Journal of Biotechnology. 133:424-432., which is incorporated hereinto by reference.

The present invention also relates to a recombinant vector, which comprises: (a) a vector, and (b) a nucleotide molecule comprising at least one of the following nucleotide sequences: (b1) a nucleotide sequence encoding xylanase and having a sequence homology of at least 80% to the nucleotide sequence of SEQ ID NO:1, and (b2) a nucleotide sequence encoding a secreting protein signal peptide and having a sequence homology of at least 80% to the nucleotide sequence of SEQ ID NO:2. Herein, the nucleotide sequence encoding xylanase (i.e., the nucleotide sequence of (b1)) and the nucleotide sequence encoding the secreting protein signal peptide (i.e., the nucleotide sequence of (b2)) are as described above.

In addition, the vector (a) is an expression vector, which is a linear or cyclic nucleotide molecule and is linked to the nucleotide molecule (b). The vector (a) can comprise segment(s) promoting transcription of the nucleotide molecule (b).

The vector in the recombinant vector of the present invention can be any vector known in the art or commercially available, as long as it is replicable and functions well in host cells. For example, when *Pichia methanolica* is used as a host cell, vectors may be pMET A, pMET B, pMET C, pMETαA, pMETαB, pMETαC, and so on from Invitrogen Co.

In the recombinant vector of the present invention, when the nucleotide sequence (b2) is combined with a nucleotide sequence of a target protein (such as the nucleotide sequence (1)) to produce the target protein (such as xylanase), by the mechanism described above, the amount of the target protein secreted to the extracellular space can be increased, thereby, increasing the extracellular expression level of the target protein.

The present invention also provides a *Pichia methanolica* host cell, which comprises the nucleotide molecule or recombinant vector of the present invention. In one embodiment of the present invention, *Pichia methanolica* is used to construct host cells, and xylanase gene Xyn11B' (SEQ ID NO:3) is modified accordingly to raise the expression level of xylanase.

The present invention further provides a method for producing xylanase, which is performed using a recombinant vector expressing xylanase, comprising the following steps: (1) transforming a recombinant vector expressing xylanase to a *Pichia methanolica* host cell; and (2) incubating the *Pichia methanolica* host cell to express xylanase. Herein, the recombinant vector and *Pichia methanolica* host cell are as described above.

In step (1), the vector can be transformed into the host cell by any known molecular biological techniques, such as a PEG protoplast method, chemical method, electroporation method, gene gun transformation method, etc.

In an embodiment, a chemical method and electroporation method are used for transformation. Herein, a suitable chemical method includes lithium acetate method and calcium chloride method, which are conducted by adding a great amount of lithium acetate or calcium chloride into a reaction solution comprising host cells. The high concentration of cations (i.e., lithium ions or calcium ions) and anions (i.e., acetate or chloride ions) in the reaction solution destroys the electric equilibrium of cell membrane of the host cells and changes the structure of cell membrane, allowing a heterologous gene to easily enter the host cells. In the electroporation method, as a cell is stimulated with an electric current, the permeability of the cell membrane would suddenly increase, allowing a heterologous gene to enter the host cells. Generally, the chemical method and electroporation method are easy and simple in terms of operation, and are suitable for various types of cells, and the success rate of transformation is high.

Various fermentation techniques known to people skilled in the art of microbiology can be used to conduct the incubation process in step (2) of the method of the present invention. For example, when a host cell is constructed using methylotrophic yeast (such as *Pichia methanolica*), fermentation can be induced with methanol to further enhance the expression level of xylanase.

Hereinafter, the present invention will be further illustrated with reference to the following examples. However, these examples are only provided for illustration purposes, and are not to limit the scope of the present invention.

EXAMPLES

Example 1

Construction of Xylanase Expression Vectors

The codon usage probability of *Pichia methanolica* was analyzed, and a modified xylanase gene of rumen fungi (i.e., a xylanase gene comprising the nucleotide sequence of SEQ ID NO:1 (i.e., coXyn11B' gene)) was synthesized, and the synthesized gene was cloned into a pCR4 preservation vector and preserved in *E. coli* ECOS101™.

Prior to the construction of expression vectors, coXyn11B' gene (SEQ ID NO:1; a 720 bp fragment) in the pCR4-coXyn11B' preservation vector was cut using restriction enzymes 5'EcoR I and 3'BamH I, and was cloned into a pMETαA expression vector (from Invitrogen Co.) to complete the construction of pMETαA-coXyn11B' expression vector, which was then preserved in *E. coli* ECOS101™.

Example 2

Construction of Xylanase Expression Vectors Comprising a Gene of Secreting Protein Signal Peptide The codon usage probability of *Pichia methanolica* was analyzed, and a modified gene encoding secreting protein signal peptide of *Saccharomyces cerevisiae* (i.e., a gene of secreting protein signal peptide comprising the nucleotide sequence of SEQ ID NO:2 (i.e., coαF gene)) was synthesized, and the synthesized gene was cloned into a pUC57 preservation vector and preserved in *E. coli* ECOS101™.

Prior to the construction of expression vectors, coαF gene (SEQ ID NO:2; a 267 bp fragment) in the pUC57-coαF preservation vector was cut by restriction enzymes 5'Sac 1 and 3'EcoR I, and was cloned into the pMETαA-coXyn11B' expression vector prepared from Example 1 to complete a pMETcoαF-coXyn11B' expression vector, which was preserved in *E. coli* ECOS101™.

Example 3

Analysis of the Nucleotide Sequences and Amino Acid Sequences of coXyn11B' (SEQ ID NO:1) and coαF (SEQ ID NO:2)

Figure 1:
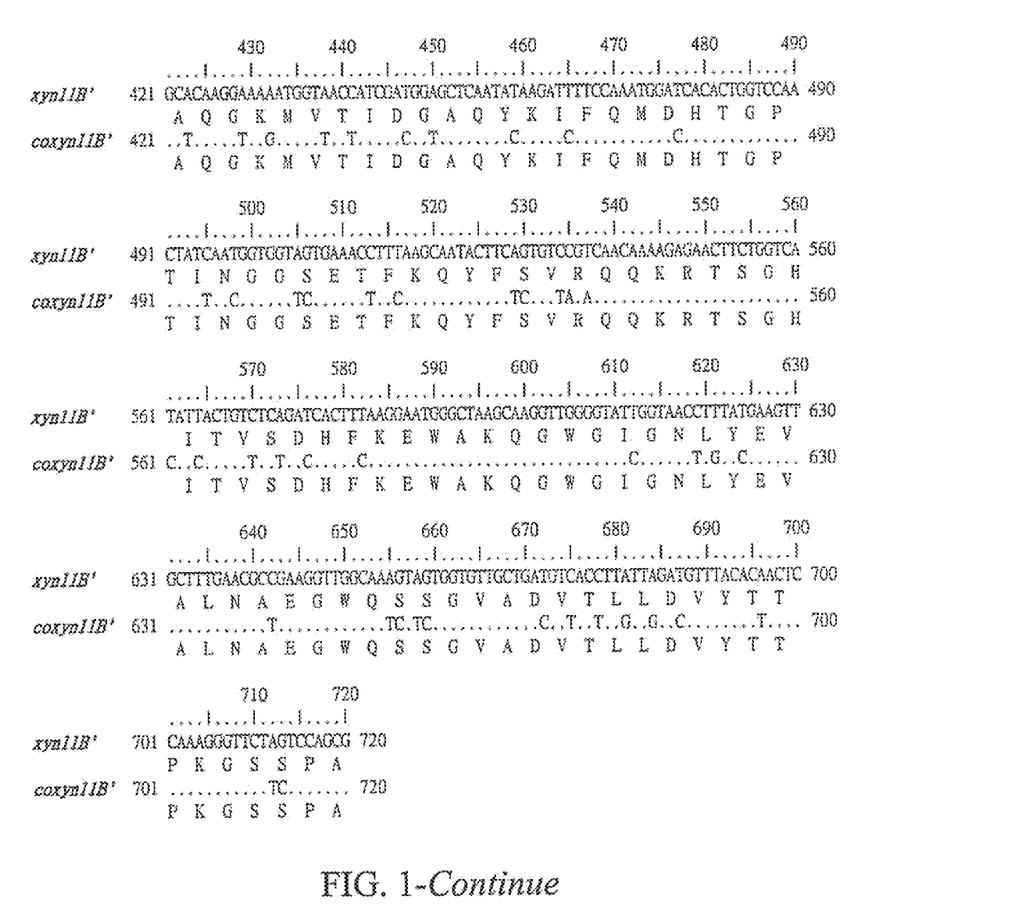
FIG. 1 is a diagram showing the comparison of the nucleotide sequences and amino acid sequences between the original xylanase Xyn11B' and gene-optimized xylanase coXyn11B', wherein the nucleotide sequence and amino acid sequence of coXyn11B' are SEQ ID NO:1 and SEQ ID NO:5, respectively; and the nucleotide sequence and amino acid sequence of Xyn11B' are SEQ ID NO:3 and SEQ ID NO:7, respectively.

A sequence comparison software, BioEdit Sequence Alignment Editor, was used to compare the nucleotide sequence and amino acid sequence of xylanase Xyn11B' (SEQ ID NO:3 and SEQ ID NO:7) and those of coXyn11B' (SEQ ID NO:1 and SEQ ID NO:5) of rumen fungi. As shown in FIG. 1, the comparison between sequences of original Xyn11B' (SEQ ID NO:3 and SEQ ID NO:7) and gene-optimized coXyn11B' (SEQ ID NO:1 and SEQ ID NO:5) demonstrated that changes only occurred on the bases of selected nucleotides in the nucleotide sequence of coXyn11B' (SEQ ID NO:1), and no change was observed in the translated amino acid sequence (i.e., no difference was observed in SEQ ID NO:5 and SEQ ID NO:7).

Figure 2:
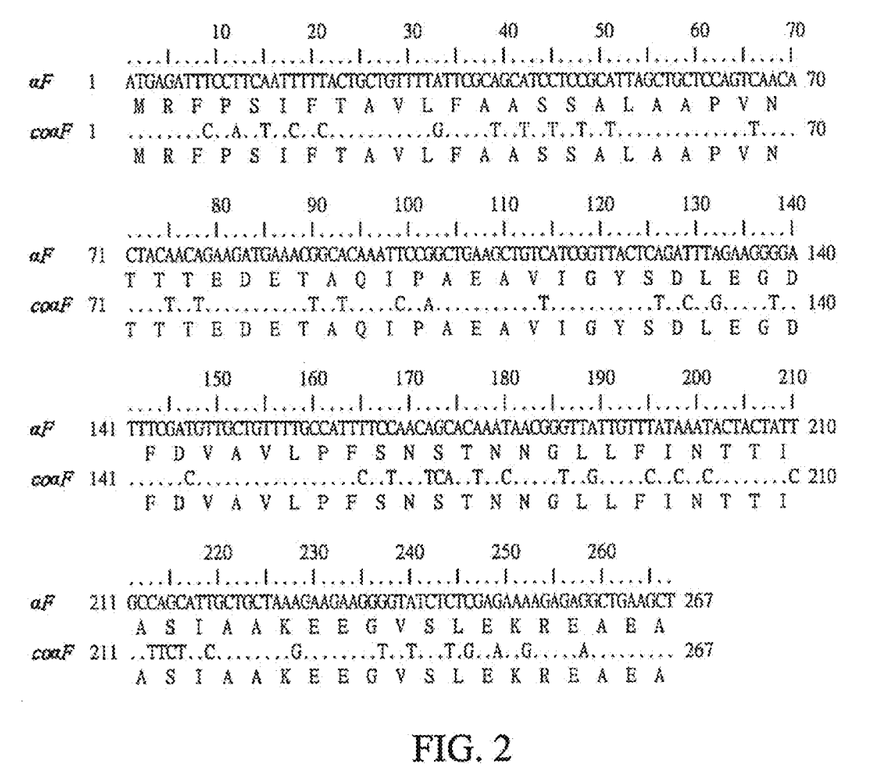
FIG. 2 is a diagram showing the comparison of the nucleotide sequences and amino acid sequences between the original secreting protein signal peptide αF and gene-optimized secreting protein signal peptide coαF, wherein the nucleotide sequence and amino acid sequence of coαF are SEQ ID NO:2 and SEQ ID NO:6, respectively; and the nucleotide sequence and amino acid sequence of αF are SEQ ID NO:4 and SEQ ID NO:8, respectively.

Similarly, the sequence comparison software, BioEdit Sequence Alignment Editor, was used to compare the nucleotide sequence and amino acid sequence of secreting protein signal peptide αF (SEQ ID NO:4 and SEQ ID NO:8) and those of coαF (SEQ ID NO:2 and SEQ ID NO:6) of *saccharomyces cerevisiae*. As shown in FIG. 2, the comparison between sequences of original αF (SEQ ID NO:4 and SEQ ID NO:8) and gene-optimized coαF (SEQ ID NO:2 and SEQ ID NO:6) demonstrated that changes only occurred on the bases of selected nucleotides in the nucleotide sequence of coαF (SEQ ID NO:2), and no change was observed in the translated amino acid sequence (i.e., no difference was observed in SEQ ID NO:6 and SEQ ID NO:8).

Example 4

Expression of Xylanase

I. Transformation of *Pichia methanolica* by Lithium Acetate Method and Electroporation Method

*Pichia methanolica* (PMAD11 competent cells) were grown in YPAD medium (containing 1 wt % yeast extract, 2 wt % peptone, 0.01 wt % adenine, and 2 wt % dextrose). First, PMAD11 competent cells were treated with a lithium acetate solution (containing 100 mM lithium acetate solution, 10 mM DTT, 0.6 M sorbital, and 10 mM tris(hydroxymethyl)aminomethane-HCl (Tris-HCl) at pH 7.5) for 30 minutes, and then dissolved in 1 ml of 1 M sorbital for preservation. A linear nucleotide molecule (20 µl) (i.e., the pMETαA-Xyn11B' expression vector or the expression vectors prepared from Example 1 and Example 2) was added to 80 µl of the competent cells, and then the mixture was transferred into an electroporation cuvette with a diameter of 0.2 cm to perform electroporation. Pulse conditions are as follows: 1,500 V, 25 µF, and 200Ω. After completion of the pulse, the competent cells were placed into 1 ml of YPDS medium (containing 1 wt % yeast extract, 2 wt % peptone, 2 wt % dextrose, and 1 M sorbital), and cultivated at 300 rpm for 2 hours. Afterwards, the cultured competent cells were coated on MD medium (minimal dextrose medium, containing 1.34 wt % YNB (yeast nitrogen base), $4 \times 10^{-5}$ vol % biotin, 1 wt % dextrose, and 2 wt % agarose), and *Pichia methanolica* comprising the pMETαA-Xyn11B', pMETαA-coXyn11B' or pMETcoαF-coXyn11B' expression vectors were obtained.

II. Screening of Transformants with High Activity

*Pichia methanolica* (200 nl) obtained from the above steps was seeded in a 96-well plate containing YPAD medium and incubated. After growth of *Pichia methanolica*, 10 µl of broth was dropped onto an MMX (methanol medium xylan) plate containing a xylan substrate (containing 1.34 wt % YNB, $4 \times 10^{-5}$ vol % biotin, 1 wt % methanol, 0.3 wt % oat spelts xylan, and 2 wt % agarose). Congo red dyeing was conducted after *Pichia methanolica* was induced by methanol for three days, transformants with high activity showing larger transparent ring were selected and inoculated to MD screening medium. After 48 hours of culture at 30° C., a single colony was selected and inoculated to YPD medium (containing 1 wt % yeast extract, 2 wt % peptone, and 2 wt % dextrose), and was cultured overnight (no more than 24 hours) at 300 rpm. Then, the cultivated transformant was mixed with an equal volume of 20% glycerol, and stored at −80° C. In the following experiments, this frozen transformant was used as seed culture. *Pichia methanolica* transformants with high activity comprising the pMETαA-Xyn11B' (Transformant 1), pMETαA-coXyn11B' (Transformants 2 to 4), or pMETcoαF-coXyn11B'(Transformant 5) expression vector were thus obtained.

The *Pichia methanolica* host cell comprising the pMETcoαF-coXyn11B' expression vector with a high expression level of xylanase (i.e., Transformant 5) was deposited in DSMZ (Deutsche Sammlung von Mikroorganismen and Zellkulturen GmbH) at Inhoffenstraβe 7B, 38124 Braunschweig, Germany on Jan. 15, 2010, wherein the deposit number was designated as DSM 23237. This deposit was made under the provisions of the Budapest Treaty on the International Recognition of the Deposit of Microorganisms for the Purposes of Patent Procedure.

III. Cultivation in Fermentation Tanks or Flasks

Prior to fermentation, 1 vol % of the frozen storage transformant was inoculated and activated in 3 ml YPD culture medium, and was cultured at 30° C., 300 rpm overnight.

Then, 1 vol % of broth was collected and inoculated in 100 ml YPD culture medium, and was cultured until late-log phase (about 20 hours).

After that, 100 ml of the broth was collected and inoculated in 2 liter Fermentation base salts (containing 2% dextrose and 4.35 ml/L PTM1 minor elements) medium, and cultured in fermentation tanks or flasks, respectively. Herein, in Group A, Transformants 1 to 4 were grown in batch culture in flasks, and in Group B, Transformants 1, 3 and 5 were grown in batch culture in fermentation tanks. Culture conditions are as follows: 30° C. and 800 rpm, the medium was maintained at pH 5 using 2 N sulfuric acid and 10% ammonia water, and aeration rate from 2 to 4 v.v.m (gas volume flow per unit of liquid volume per minute).

After about 20 hours of culture, as dissolved oxygen value apparently increased or the fungi no longer produced acid (i.e., adding base to maintain pH value was no longer required), the fungi had fully used the carbon source. As that time, methanol (1 liter methanol comprising 12 ml/L PTM1 minor elements) was used to induce the generation of xylanase.

In Group A, fermentation was ended after 120 hours of culture of Transformants 1 to 4, and in Group B, fermentation was ended after 72 or 192 hours of culture of Transformants 1, 3 and 5. Thereafter, the broth was collected and centrifuged, and the supernatant was collected to obtain a crude xylanase solution.

Example 5

Xylanase Activity Test

Xylanase activity was measured by the following mechanism: a dinitrosalicylic acid (DNS) solution was heated together with reducing sugars produced by xylanase hydrolysis to form brownish red amino compounds, and xylanase activity was determined by the amount of reducing sugars in samples, which was measured using color comparimetry. This method can be seen in Georis et al. 1999. Sequence, overproduction and purification of the family 11 endo-beta-1,4-xylanase encoded by the xyl1 gene of Streptomyces sp. S38. Gene 237:123-33., which is incorporated hereinto by reference.

First, the crude xylanase solution acquired from Example 4 (after 120 hours (Group A) or 192 hours (Group B) of culture) was adjusted to an appropriate concentration. Thereafter, 40 µl crude xylanase solution was mixed with 360 µl 1% xylan substrate solution (containing 3 wt % xylan (oat spelts xylan dissolved in 25 mM of tris(hydroxymethyl)aminomethane (or Tris) buffer at pH 8.0), and after a reaction at 60° C. for 5 minutes, a DNS reagent was added to terminate the reaction, and then the mixture reacted for another 5 minutes at 98° C. for coloring. Lastly, the absorbance was measured at a wavelength of 540 nm, and the amount of reducing sugars was calculated to determine xylanase activity. Test results are shown in Table 1 and Table 2. Herein, 1 activity unit (U) is defined as the amount of enzyme needed to release/hydrolyze 1 µmole of reducing sugars per ml per minute.

TABLE 1

| | | Group A | | |
|---|---|---|---|---|
| Expression vector | Signal peptide gene (α-factor) | Xylanase gene | Xylanase activity (U/ml) | Increase in enzyme activity (fold) |
| pMETαA-Xyn11B' (Transformant 1) | original (Wild type) | original (Xyn11B'; SEQ ID NO: 3) | 565 ± 24 | 1 |
| pMETαA-coXyn11B' (Transformant 2) | original | optimized (coXyn11B'; SEQ ID NO: 1) | 3,975 ± 78 | 7.0 |
| pMETαA-coXyn11B' (Transformant 3) | original | optimized (coXyn11B'; SEQ ID NO: 1) | 4,692 ± 172 | 8.3 |
| pMETαA-coXyn11B' (Transformant 4) | original | optimized (coXyn11B'; SEQ ID NO: 1) | 3,843 ± 199 | 6.8 |

The results of xylanase activity test in Table 1 demonstrated that after 120 hours culture in the flasks, the activity of xylanase expressed by the transformant comprising original Xyn11B' gene (SEQ ID NO:3) was 565±24 U/ml; the activity of xylanase expressed by the transformant comprising gene-optimized coXyn11B' gene (SEQ ID NO:1) was 3,843±199 to 4,692±172 U/ml.

TABLE 2

| | | Group B | | |
|---|---|---|---|---|
| Expression vector | Signal peptide gene (α-factor) | Xylanase gene | Xylanase activity (U/ml) | Increase in enzyme activity (fold) |
| pMETαA-Xyn11B' (Transformant 1) | original | original (Xyn11B'; SEQ ID NO: 3) | 4,251 ± 242 | 1 |
| pMETαA-coXyn11B' (Transformant 3) | original | optimized (coXyn11B'; SEQ ID NO: 1) | 20,654 ± 1,560 | 4.9 |
| pMETcoαF-coXyn11B' (Transformant 5) | optimized (coαF, SEQ ID NO: 2) | optimized (coXyn11B'; SEQ ID NO: 1) | 38,740 ± 543 | 9.1 |

The results of xylanase activity test in Table 2 demonstrated that after 192 hours culture in fermentation tanks, xylanase activity of the transformant comprising original Xyn11B' gene (SEQ ID NO:3) was 4,251±242 U/ml; xylanase activity of the transformant comprising gene-optimized coXyn11B' gene (SEQ ID NO:1) was 20,654±1,560 U/ml; and xylanase activity of the transformant comprising optimized xylanase gene combined with optimized gene of secreting protein signal peptide, i.e., coαF (SEQ ID NO:2)-coXyn11B' (SEQ ID NO:1) gene, was up to 38,740±543 U/ml.

Example 6

Protein Electrophoresis Analysis of Xylanase Expression

Xylanase expressed by the transformants prepared in Group B of Example 4 comprising the original Xyn11B' gene (SEQ ID NO:3) (i.e., Transformant 1), gene-optimized coXyn11B' gene (SEQ ID NO:1) (i.e., Transformant 3), and optimized xylanase gene combined with optimized gene of the secreting protein signal peptide coαF (SEQ ID NO:2)-coXyn11B' (SEQ ID NO:1) (i.e., Transformant 5) was applied to sodium dodecyl sulfate-polyacrylamide gel electrophoresis (SDS-PAGE) analysis (see Sambrook et al. 2001. Molecular Cloning: SDS-polyacrylamide gel electrophoresis of protein. Third edition: A8. 40-49., which is incorporated hereinto by reference).

Figure 3:
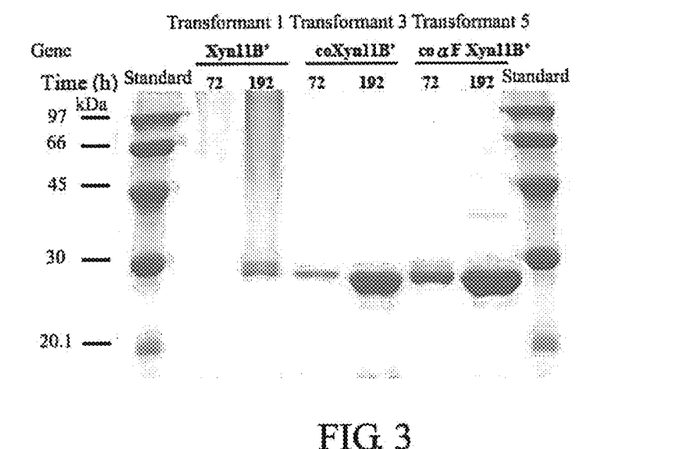
FIG. 3 is a protein electrophoresis diagram showing xylanase expressed by the transformants comprising the Xyn11B' gene (SEQ ID NO:3), coXyn11B' gene (SEQ ID NO:1) or coαF (SEQ ID NO:2)-coXyn11B' gene (SEQ ID NO:1).

As shown in FIG. 3, the protein electrophoresis analysis demonstrated that the molecular weight of xylanase is about 29 kDa, and after 72 hours of culture, there was no obvious protein signal for the transformant comprising the original Xyn11B' gene (SEQ ID NO:3); however, there was an obvious protein signal for the transformants comprising the coXyn11B' gene (SEQ ID NO:1) or coαF (SEQ ID NO:2)-coXyn11B' (SEQ ID NO:1) gene.

In addition, after 192 hours of culture, a significantly higher expression level of xylanase can be seen in the transformant comprising the coXyn11B' gene (SEQ ID NO:1) or coαF (SEQ ID NO:2)-coXyn11B' (SEQ ID NO:1) gene as compared to the transformant comprising the original Xyn11B' gene (SEQ ID NO:3). Moreover, a significantly higher expression level of xylanase can be seen in the transformant comprising the coαF (SEQ ID NO:2)-coXyn11B' (SEQ ID NO:1) gene in comparison with the transformant comprising the coXyn11B' gene (SEQ ID NO:1).

The results of Example 5 and Example 6 demonstrated that using the modified nucleotide molecule of the present invention to produce xylanase can elevate the expression level of xylanase in *Pichia methanolica* host cells. In addition, the nucleotide molecule combined with a modified gene of a secreting protein signal peptide of the present invention can further increase the synthesis rate of xylanase, which can be secreted to the extracellular space, thereby the extracellular expression level was enhanced.

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. An isolated nucleotide molecule comprising a nucleotide sequence of SEQ ID NO:1, which encodes a xylanase.

2. The nucleotide molecule as claimed in claim 1, which further comprises a nucleotide sequence encoding a secreting protein signal peptide and having a sequence homology of at least 80% to the nucleotide sequence of SEQ ID NO:2.

3. The nucleotide molecule as claimed in claim 2, wherein the nucleotide sequence encoding the secreting protein signal peptide has a sequence homology of at least 85% to the nucleotide sequence of SEQ ID NO:2.

4. The nucleotide molecule as claimed in claim 2, wherein the nucleotide sequence encoding the secreting protein signal peptide has a sequence homology of at least 90% to the nucleotide sequence of SEQ ID NO:2.

5. A recombinant vector comprising:
   (a) a vector; and
   (b) a nucleotide molecule comprising:
      (b1) a nucleotide sequence of SEQ ID NO:1, which encodes a xylanase.

6. A method for producing xylanase comprising:
   (1) transforming a recombinant vector expressing xylanase to a *Pichia methanolica* host cell; and
   (2) incubating the *Pichia methanolica* host cell to express xylanase,
   wherein the recombinant vector expressing xylanase comprises:
      (a) a vector; and
      (b) a nucleotide molecule, comprising (b1) a nucleotide sequence of SEQ ID NO:1, which encodes a xylanase.

7. The method as claimed in claim 6, wherein the nucleotide molecule further comprises (b2) a nucleotide sequence encoding a secreting protein signal peptide and having a sequence homology of at least 80% to the nucleotide sequence of SEQ ID NO:2.

8. The method as claimed in claim 7, wherein the nucleotide sequence encoding the secreting protein signal peptide has a sequence homology of at least 85% to the nucleotide sequence of SEQ ID NO:2.

9. The method as claimed in claim 7, wherein the nucleotide sequence encoding the secreting protein signal peptide has a sequence homology of at least 90% to the nucleotide sequence of SEQ ID NO:2.

10. The recombinant vector as claimed in claim 5, wherein the nucleotide molecule further comprises (b2) a nucleotide sequence encoding a secreting protein signal peptide and having a sequence homology of at least 80% to the nucleotide sequence of SEQ ID NO:2.

11. The recombinant vector as claimed in claim 10, wherein the nucleotide sequence encoding the secreting protein signal peptide has a sequence homology of at least 85% to the nucleotide sequence of SEQ ID NO:2.

12. The recombinant vector as claimed in claim 10, wherein the nucleotide sequence encoding the secreting protein signal peptide has a sequence homology of at least 90% to the nucleotide sequence of SEQ ID NO:2.

* * * * *

SEQUENCE LISTING

```
<160> NUMBER OF SEQ ID NOS: 8

<210> SEQ ID NO 1
<211> LENGTH: 720
<212> TYPE: DNA
<213> ORGANISM: Artificial Sequence
<220> FEATURE:
<223> OTHER INFORMATION: Modified xylanase DNA sequence from
      Neocallimastix frontalis

<400> SEQUENCE: 1
actgttgcta aggctcaatg gggtggtggt gcttctgctg gtcaaaagtt gtctgttggt      60
ggtggtcaaa accaacacaa gggtgtttct gacggtttct cttacgaaat ctggttggac     120
aacactggtg gttctggttc tatgactttg ggttctggtg ctactttcaa ggctgaatgg     180
aacgctgctg ttaacagagg taacttcttg gctagaagag gtttagactt cggttctcaa     240
aagaaggcta ctgactactc ttacatcggt ttagactaca ctgctactta cagacaaact     300
gcttctgctt ctggtaactc tagattgtgt gtttacggtt ggttccaaaa cagaggtgtt     360
caaggtgttc cattggttga atactacatc atcgaagatt gggttgactg ggttccagat     420
gctcaaggta agatggttac tatcgacggt gctcaataca agatcttcca aatggaccac     480
actggtccaa ctattaacgg tggttctgaa actttcaagc aatacttctc tgttagacaa     540
caaaagagaa cttctggtca catcactgtt tctgaccact tcaaggaatg ggctaagcaa     600
ggttggggta tcggtaactt gtacgaagtt gctttgaacg ctgaaggttg gcaatcttct     660
ggtgttgctg acgttacttt gttggacgtt tacactactc caaagggttc ttctccagcg     720
```

<210> SEQ ID NO 2
<211> LENGTH: 267
<212> TYPE: DNA
<213> ORGANISM: Artificial Sequence
<220> FEATURE:
<223> OTHER INFORMATION: Modified DNA sequence of secreting protein
      signal peptide from Saccharomyces cerevisiae

<400> SEQUENCE: 2
atgagattcc catctatctt cactgctgtt ttgttcgctg cttcttctgc tttagctgct        60
ccagttaaca ctactactga agatgaaact gctcaaatcc cagctgaagc tgttatcggt       120
tactctgact tggaaggtga tttcgacgtt gctgttttgc cattctctaa ctcaactaac       180
aacggtttgt tgttcatcaa cactactatc gcttctatcg ctgctaagga agaaggtgtt       240
tctttggaaa agagagaagc tgaagct                                          267

<210> SEQ ID NO 3
<211> LENGTH: 720
<212> TYPE: DNA
<213> ORGANISM: Neocallimastix frontalis

<400> SEQUENCE: 3
actgttgcta aggcccaatg gggtggaggt gcttccgctg gtcaaaaatt atccgtcggt        60
ggtggtcaaa accaacataa gggtgtctcc gatggtttca gttatgaaat ctggttagat       120
aacaccggtg gtagcggttc tatgactctc ggtagtggtg caaccttcaa ggctgaatgg       180
aatgcagctg ttaaccgtgg taacttcctt gcccgtcgtg gtcttgactt cggttctcaa       240
aagaaggcaa ccgattacag ctacatcgga ttggattata ctgcaactta cagacaaact       300
gccagtgcaa gtggtaactc ccgtctctgt gtatacggat ggttccaaaa ccgtggagtt       360
caaggcgttc ctttagtaga atactacatc attgaagatt gggttgactg ggttccagat       420
gcacaaggaa aaatggtaac catcgatgga gctcaatata agatttttcca aatggatcac       480 actggtccaa ctatcaatgg tggtagtgaa acctttaagc aatacttcag tgtccgtcaa       540
caaaagagaa cttctggtca tattactgtc tcagatcact ttaaggaatg ggctaagcaa       600
ggttggggta ttggtaacct ttatgaagtt gctttgaacg ccgaaggttg gcaaagtagt       660
ggtgttgctg atgtcacctt attagatgtt tacacaactc caagggttc tagtccagcg       720

<210> SEQ ID NO 4
<211> LENGTH: 267
<212> TYPE: DNA
<213> ORGANISM: Saccharomyces cerevisiae

<400> SEQUENCE: 4
atgagatttc cttcaatttt tactgctgtt ttattcgcag catcctccgc attagctgct        60
ccagtcaaca ctacaacaga agatgaaacg gcacaaattc cggctgaagc tgtcatcggt       120
tactcagatt tagaagggga tttcgatgtt gctgttttgc cattttccaa cagcacaaat       180
aacgggttat tgtttataaa tactactatt gccagcattg ctgctaaaga agaaggggta       240
tctctcgaga aaagagaggc tgaagct                                          267

<210> SEQ ID NO 5
<211> LENGTH: 240
<212> TYPE: PRT
<213> ORGANISM: Artificial Sequence
<220> FEATURE:
<223> OTHER INFORMATION: Xylanase protein sequence from the modification
      of native xylanase DNA sequence of Neocallimastix frontalis

<400> SEQUENCE: 5

```
Thr Val Ala Lys Ala Gln Trp Gly Gly Ala Ser Ala Gly Gln Lys
 1               5                   10                  15

Leu Ser Val Gly Gly Gly Gln Asn Gln His Lys Gly Val Ser Asp Gly
            20                  25                  30

Phe Ser Tyr Glu Ile Trp Leu Asp Asn Thr Gly Gly Ser Gly Ser Met
        35                  40                  45

Thr Leu Gly Ser Gly Ala Thr Phe Lys Ala Glu Trp Asn Ala Ala Val
    50                  55                  60

Asn Arg Gly Asn Phe Leu Ala Arg Arg Gly Leu Asp Phe Gly Ser Gln
 65                 70                  75                  80

Lys Lys Ala Thr Asp Tyr Ser Tyr Ile Gly Leu Asp Tyr Thr Ala Thr
                85                  90                  95

Tyr Arg Gln Thr Ala Ser Ala Ser Gly Asn Ser Arg Leu Cys Val Tyr
            100                 105                 110

Gly Trp Phe Gln Asn Arg Gly Val Gln Gly Val Pro Leu Val Glu Tyr
        115                 120                 125

Tyr Ile Ile Glu Asp Trp Val Asp Trp Val Pro Asp Ala Gln Gly Lys
    130                 135                 140

Met Val Thr Ile Asp Gly Ala Gln Tyr Lys Ile Phe Gln Met Asp His
145                 150                 155                 160

Thr Gly Pro Thr Ile Asn Gly Gly Ser Glu Thr Phe Lys Gln Tyr Phe
                165                 170                 175

Ser Val Arg Gln Gln Lys Arg Thr Ser Gly His Ile Thr Val Ser Asp
            180                 185                 190

His Phe Lys Glu Trp Ala Lys Gln Gly Trp Gly Ile Gly Asn Leu Tyr
        195                 200                 205

Glu Val Ala Leu Asn Ala Glu Gly Trp Gln Ser Ser Gly Val Ala Asp
    210                 215                 220

Val Thr Leu Leu Asp Val Tyr Thr Thr Pro Lys Gly Ser Ser Pro Ala
225                 230                 235                 240
```

<210> SEQ ID NO 6
<211> LENGTH: 89
<212> TYPE: PRT
<213> ORGANISM: Artificial Sequence
<220> FEATURE:
<223> OTHER INFORMATION: Secreting protein signal peptide protein
      sequence from the modification of native secreting protein signal
      peptide DNA sequence of Saccharomyces cerevisiae

<400> SEQUENCE: 6

```
Met Arg Phe Pro Ser Ile Phe Thr Ala Val Leu Phe Ala Ala Ser Ser
 1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
 65                 70                  75                  80

Ser Leu Glu Lys Arg Glu Ala Glu Ala
                85
```

```
<210> SEQ ID NO 7
<211> LENGTH: 240
<212> TYPE: PRT
<213> ORGANISM: Neocallimastix frontalis

<400> SEQUENCE: 7

Thr Val Ala Lys Ala Gln Trp Gly Gly Ala Ser Ala Gly Gln Lys
1               5                   10                  15

Leu Ser Val Gly Gly Gln Asn Gln His Lys Gly Val Ser Asp Gly
            20                  25                  30

Phe Ser Tyr Glu Ile Trp Leu Asp Asn Thr Gly Gly Ser Gly Ser Met
        35                  40                  45

Thr Leu Gly Ser Gly Ala Thr Phe Lys Ala Glu Trp Asn Ala Ala Val
50                  55                  60

Asn Arg Gly Asn Phe Leu Ala Arg Arg Gly Leu Asp Phe Gly Ser Gln
65                  70                  75                  80

Lys Lys Ala Thr Asp Tyr Ser Tyr Ile Gly Leu Asp Tyr Thr Ala Thr
                85                  90                  95

Tyr Arg Gln Thr Ala Ser Ala Ser Gly Asn Ser Arg Leu Cys Val Tyr
            100                 105                 110

Gly Trp Phe Gln Asn Arg Gly Val Gln Gly Val Pro Leu Val Glu Tyr
        115                 120                 125

Tyr Ile Ile Glu Asp Trp Val Asp Trp Val Pro Asp Ala Gln Gly Lys
130                 135                 140

Met Val Thr Ile Asp Gly Ala Gln Tyr Lys Ile Phe Gln Met Asp His
145                 150                 155                 160

Thr Gly Pro Thr Ile Asn Gly Gly Ser Glu Thr Phe Lys Gln Tyr Phe
                165                 170                 175

Ser Val Arg Gln Gln Lys Arg Thr Ser Gly His Ile Thr Val Ser Asp
            180                 185                 190

His Phe Lys Glu Trp Ala Lys Gln Gly Trp Gly Ile Gly Asn Leu Tyr
        195                 200                 205

Glu Val Ala Leu Asn Ala Glu Gly Trp Gln Ser Ser Gly Val Ala Asp
210                 215                 220

Val Thr Leu Leu Asp Val Tyr Thr Thr Pro Lys Gly Ser Ser Pro Ala
225                 230                 235                 240

<210> SEQ ID NO 8
<211> LENGTH: 89
<212> TYPE: PRT
<213> ORGANISM: Saccharomyces cerevisiae

<400> SEQUENCE: 8

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala
                85
```